(12) United States Patent
Balaban et al.

(10) Patent No.: US 6,689,878 B2
(45) Date of Patent: Feb. 10, 2004

(54) TARGET OF RNAIII ACTIVATING PROTEIN (TRAP)

(75) Inventors: Naomi Balaban, Davis, CA (US); Tzipora Goldkorn, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 111 days.

(21) Appl. No.: 09/953,780

(22) Filed: Sep. 12, 2001

(65) Prior Publication Data

US 2002/0102271 A1 Aug. 1, 2002

Related U.S. Application Data

(62) Division of application No. 09/393,862, filed on Sep. 10, 1999.
(60) Provisional application No. 60/100,415, filed on Sep. 15, 1998.

(51) Int. Cl.[7] .................. C07H 21/04; C12P 21/06; C12N 5/00; C12N 15/00
(52) U.S. Cl. .................. 536/23.5; 435/69.1; 435/325; 435/320.1
(58) Field of Search .................. 536/23.5; 435/320.1, 435/325, 69.1

(56) References Cited

FOREIGN PATENT DOCUMENTS

| WO | WO 96/10579 | 4/1996 |
| WO | WO 97/44349 | 11/1997 |

OTHER PUBLICATIONS

EP786519A2 (Barash et al.) Jul. 30, 1997, Abstract & nucleic acid comparison only.*
Cassady et al. (PRI Database, NCBI, Aug. 20, 1997).*
Contig906, Blast Search Results, "OU *Staphylococcus aureus* Sequence Blast Server Results," Conducted on Jul. 22, 1999.
Balaban et al. (Apr. 1998), "Autoinducer of Virulence as a Target for Vaccine and Therapy Against *Staphylococcus aureus*," *Science*, vol. 280:438–440.
Balaban et al. (Feb. 1995), "Autocrine Regulation of Toxin Synthesis by *Staphylococcus aureus*," *Proc. Natl. Acad. Sci. USA*, vol. 92:1619–1623.
Bayer et al. (Aug. 1996), "The Molecular Architecture of the Sar Locus in *Staphylococcus aureus*," *Journal of Bacteriology*, vol. 178(15):4563–4570.
Chien et al. (Jan. 1998), "Molecular Interactions between Two Global Regulators, Sar and Agr, in *Staphylococcus aureus*," *Journal of Biological Chemistry*, vol. 273(5):2645–2652.
Ji et al. (Dec. 1995), "Cell Density Control of Staphylococcal Virulence Mediated by an Octapeptide Pheromone," *Proc. Natl. Acad. Sci. USA*, vol. 92:12055–12059.
Ji et al. (Jun. 1997), "Bacterial Interface Caused by Autoinducing Peptide Variants," *Science*, vol. 276:2027–2030.
Lina et al. (1998), "Transmembrane Topology and Histidine Protein Kinase Activity of AgrC, The Agr Signal Recpetor in *Staphylococcus aureus*," *Molecular Microbiology*, vol. 28(3):655–662.
Lowy (Aug. 1998), "*Staphylococcus aureus* Infections," *New England Journal of Medicine*, vol. 339(8):520–532.
Mayville et al. (Feb. 1999), "Structure–Activity Analysis of Synthetic Autoinducing Thiolactone Peptides from *Staphylococcus aureus* Responsible for Virulence," *Proc. Natl. Acad. Sci. USA*, vol. 96:1218–1223.
Morfeldt et al. (1995), "Activation of Alpha–Toxin Translation in *Staphylococcus aureus* by the Trans–Encoded Antisense RNA, RNAIII," *EMBO Journal*, vol. 14(18):4569–4577.
Morfeldt et al. (1996), "Detection of the Response Regulator AgrA in the Cytosolic Fraction of *Staphylococcus aureus* by Monoclonal Antobodies," *FEMS Microbiology Letters*, vol. 143:195–201.
Novick et al. (1999), "Virulence Gene Regulation by Peptides in Staphylococci and Other Gram–Positive Bacteria," *Curr. Opinion Microbiol.*, vol. 2:40–45.
Novick et al. (1995), "The Agr P2 Operon: An Autocatalytic Sensory Transduction System in *Staphylococcus aureus*," *Mol. Gen Genet.*, vol. 248:446–458.
Novick et al. (1993), "Synthesis of Staphylococcal Virulence Factors is Controlled by a Regulatory RNA Molecule," *EMBO Journal*, vol. 12(10):3967–3975.
Roychoudhury et al. (Feb. 1993), "Inhibitors of Two–Component Signal Transduction Systems: Inhibition of Alginate Gene Activation in *Pseudomonas aeruginosa*," vol. 90:965–969.

* cited by examiner

*Primary Examiner*—Anthony C. Caputa
*Assistant Examiner*—Gary B. Nickol
(74) *Attorney, Agent, or Firm*—Smith, Gambrell & Russell LLP; Suzannah K. Sundby

(57) ABSTRACT

The present invention is directed to a protein isolated from *S. aureus* that is the target of RAP, called TRAP, which is characterized by a molecular weight of about 21 KDa, is capable of being phosphorylated by RAP, and comprises an amino acid sequence of SEQ ID NO:2. In addition, the present invention is directed towards an antibody immunoreactive with TRAP that is preferably a monoclonal antibody or a humanized antibody but may be a polyclonal antibody. The invention provides a method of treating *S. aureus* infection by administering such a TRAP-inhibiting agent. The invention also features methods for identifying compounds that inhibit TRAP activity and/or inhibit TRAP-RAP interaction.

23 Claims, 8 Drawing Sheets

S. aureus + 1. <3(containing octapeptide)
2. total sup (containing octapeptide+RAP)
3. RAP
4. PBS The effect of RAP and RIP on TRAP phosphorylation The effect of RAP and RIP on transcription of RNAIII

SEQUENCE LISTING

<160> NUMBER OF SEQ ID NOS: 6

<210> SEQ ID NO 1
<211> LENGTH: 567
<212> TYPE: DNA
<213> ORGANISM: Staphylococcus aureus

<400> SEQUENCE: 1

| | | | | | |
|---|---|---|---|---|---|
| taatagtggt | aatgactagt | ttatcatcgt | ataataaata | aaaacataag | ggggaccttt | 60 |
| catatgaaga | aactatatac | atcttatggc | acttatggat | ttttacatca | gataaaaatc | 120 |
| aataacccga | cccatcaact | attccaattt | tcagcatcag | atacttcagt | tatttttgaa | 180 |
| gaaactgatg | gtgagactgt | tttaaaatca | ccttcaatat | atgaagttat | taaagaaatt | 240 |
| ggtgaattca | gtgaacatca | tttctattgt | gcaatcttca | ttccatcaac | agaagatcat | 300 |
| gcatatcaac | ttgaaaagaa | actgattagt | gtagacgata | atttcagaaa | ctttggtggc | 360 |

```
tttaaaagct atcgtttgtt aagacctgct aaaggtacaa catacaaaat ttatttcgga    420
tttgctgatc gacatgcata cgaagacttt aagcaatctg atgcctttaa tgaccatttt    480
tcaaaagacg cattaagtca ttactttggt tcaagcggac aacattcaag ttattttgaa    540
agatatctat acccaataaa agaatag                                        567
```

<210> SEQ ID NO 2
<211> LENGTH: 167
<212> TYPE: PRT
<213> ORGANISM: Staphylococcus aureus

<400> SEQUENCE: 2

```
Met Lys Lys Leu Tyr Thr Ser Tyr Gly Thr Tyr Gly Phe Leu His Gln
 1               5                  10                  15

Ile Lys Ile Asn Asn Pro Thr His Gln Leu Phe Gln Phe Ser Ala Ser
            20                  25                  30

Asp Thr Ser Val Ile Phe Glu Thr Asp Gly Glu Thr Val Leu Lys
        35                  40                  45

Ser Pro Ser Ile Tyr Glu Val Ile Lys Glu Ile Gly Glu Phe Ser Glu
    50                  55                  60

His His Phe Tyr Cys Ala Ile Phe Ile Pro Ser Thr Glu Asp His Ala
65                  70                  75                  80

Tyr Gln Leu Glu Lys Lys Leu Ile Ser Val Asp Asp Phe Arg Asn
                85                  90                  95

Phe Gly Gly Phe Lys Ser Tyr Arg Leu Leu Arg Pro Ala Lys Gly Thr
            100                 105                 110

Thr Tyr Lys Ile Tyr Phe Gly Phe Ala Asp Arg His Ala Tyr Glu Asp
        115                 120                 125

Phe Lys Gln Ser Asp Ala Phe Asn Asp His Phe Ser Lys Asp Ala Leu
    130                 135                 140

Ser His Tyr Phe Gly Ser Ser Gly Gln His Ser Ser Tyr Phe Glu Arg
145                 150                 155                 160

Tyr Leu Tyr Pro Ile Lys Glu
                165
```

<210> SEQ ID NO 3
<211> LENGTH: 7
<212> TYPE: PRT
<213> ORGANISM: S. aureus
<220> FEATURE:
<221> NAME/KEY: VARIANT
<222> LOCATION: (1)...(7)
<223> OTHER INFORMATION: Xaa = Any Amino Acid

<400> SEQUENCE: 3

```
Tyr Ser Pro Xaa Thr Asn Phe
 1               5
```

<210> SEQ ID NO 4
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 4

```
Tyr Ser Pro Trp Thr Asn Phe
 1               5
```

<210> SEQ ID NO 5

-continued

```
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 5

Tyr Lys Pro Trp Thr Asn Phe
 1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 6

Tyr Lys Pro Ile Thr Asn Phe
 1               5
```

TARGET OF RNAIII ACTIVATING PROTEIN (TRAP)

CROSS REFERENCE OF RELATED APPLICATION

This application is a divisional of U.S. application serial No. 09/393,862, filed Sep. 10, 1999, now pending, which application claims the benefit of prior provisional application serial No. 60/100,415, filed Sep. 15, 1998, now abandoned, each of which applications are incorporated herein by reference in their entireties.

FIELD OF THE INVENTION

This invention relates generally to the field of proteins and methods of using such, and more specifically to proteins and portions thereof that regulate the pathway by which toxins are formed by *Staphylococcus aureus*.

BACKGROUND OF THE INVENTION

The Gram-positive, aerobic bacterial pathogen *Staphylococcus aureus* (*S. aureus*) inhabits the skin and mucous membrane of humans and other animals. *S. aureus* causes diseases ranging from minor skin infections to life-threatening infections such as pneumonia, endocarditis, meningitis, postoperative wound infections, septicemia, and toxic shock syndrome. Staphylococcus is one of the most common causes of hospital-acquired infections worldwide, and reports of its growing levels of resistance to last-resort antibiotics such as vancomycin threaten a serious international public health problem.

Pathogenic *S. aureus* causes disease mainly by the production of virulence factors such as hemolysins, enterotoxins, and toxic shock syndrome toxin. The toxins can interfere with the host's immune system and degrade tissue components such as proteins, nucleic acid, lipids, and polysaccharides. In culture, these toxins are produced only at higher cell densities (e.g., the post-exponential growth phase). At lower densities during the early exponential phase, the bacteria express surface molecules such as fibronectin binding-proteins, fibrinogen binding-proteins, and protein A, which facilitate adherence of the bacteria to host cells and thwart host immune defenses. This phenomenon of growth-phase variation allows the bacteria to adhere to host cells when in low numbers, but to "disengage" and spread when too crowded, thus allowing dissemination and spread of infection (Lowy *New Engl. J. Med.* 339:520–32 (1998)).

The growth-phase associated regulation of *S. aureus* virulence factor synthesis is controlled by a quorom sensing mechanism. The control of virulence factor production is a complex process, which apparently involves multiple global regulatory loci. One of these regulatory loci, the agr locus, contains two divergent transcription units, RNAII and RNAIII, both of which are active only from the midexponential phase of growth and are autocatalytic (Novick et al. *Mol. Gen. Genet.* 248:446058 (1995)). RNAIII, an RNA regulatory molecule encoded by the agr locus, upregulates genes encoding for toxic exomolecules while down regulating genes encoding for surface molecules, resulting in vivo in dissemination and disease (Novick et al. *EMBO J.* 12:3967–75 (1993); Balaban et al. *Proc. Natl. Acad. Sci. USA* 92:1619–23 (1995); Moerfeldt et al. *EMBO J.* 14:4569–77 (1995)). The RNAII locus regulates the expression of RNAIII. The RNAII locus comprises four open reading frames (ORFs), agrA, agrB, agrC, and agrD. The agrA and agrC genes encode for a classical two-component signal transduction pathway, with agrC encoding a signal receptor and agrA the response regulator.

The autoinducers of RNAIII that have been described to date include the agr-independent RNAIII activating protein (RAP) (Balaban et al. (1995) supra; Balaban et al. *Science* 280:438–40 (1998)), and the agrD-derived octapeptide pheromone (Ji et al. *Proc. Natl. Acad. Sci.* 92:12055–9 (1995)), which binds and activates phosphorylation of AgrC (Lina et al. *Mol. Microbiol.* 28:655–662 (1998), which in turn is thought to phosphorylate AgrA, leading to upregulation of RNAIII (Morfeldt et al., *FEMS Microbiol. Lett.* 143:195–201 (1996)). The agrD-derived octapeptide has also been shown to be part of a "bacterial interference" system that provides a mechanism for different *S. aureus* strains to compete with each other at an infection site (Ji et al. *Science* 276:2027–30 (1997)). In this bacterial interference system, the octapeptide activates RNAIII transcription of the strain by which it is produced, while also acting as an inhibitor of RNAIII transcription of other strains of Staphyloccocus.

In addition to agr, the sar locus also plays a role in regulation of *S. aureus* virulence factor production. The sar locus comprises a sarA ORF preceded by a triple promoter region interspersed with two putative smaller ORFs (ORF3 and ORF4). The triple promoter system yields three overlapping sar transcripts (sarA, sarC and sarB) (Bayer et al. *J. Bacteriol.* 178:4563–70 (1996)). The SarA protein has been shown to bind to the agr promoter region and to stimulate the transcription of RNAII (Chien et al. *J. Biol. Chem.* 273:2645–52 (1998).

In vivo *S. aureus* first produce proteins that facilitate bacterial binding to host cells as well as the secreted autoinducer molecules. As the bacterial colony increases in density, the autoinducer molecules accumulate. Upon reaching a threshold concentration, the autoinducers activate RNAIII transcription, which in turn results in virulence factor production. The virulence factors damage and eventually destroy surrounding host cells, which serve as nutritive sources for the *S. aureus* bacteria and promoting further growth of the colony. Thus, inhibition of RNAIII by suppression of the autoinducers or their receptors is of particular interest in treatment or prevention of *S. aureus*-mediated disease. Several mechanisms for RNAIII inhibition have been identified, including inhibition of RNAIII by anti-RAP antibodies and by a peptide termed the RNAIII inhibiting peptide (RIP), which competes with RAP (Balaban et al. (1995) supra). Animals vaccinated with RAP or treated with RIP have been shown to be protected from an *S. aureus* infection (Balaban et al. (1998), supra).

Identification of additional components of the *S. aureus* virulence factor regulatory system is of great interest as such will provide additional therapeutic targets. The present invention provides a newly identified component of the system that regulates virulence factor production in *S. aureus*.

REFERENCES

Roychoudhury, S. et al. *Proc. Natl. Acad. Sci. U.S.A.*, 90: 965–969 (1993) described the identification of synthetic chemical compounds that block the expression of alginate, a virulence factor for the cystic fibrosis pathogen *Pseudomonas aeruginosa*. However, it has not been shown that the small molecules would have any effect on *S. aureus*, or offer potential clinical utility.

Balaban et al. *Proc. Natl. Acad. Sci. USA* 92:1619–23 (1995) reports autocrine regulation of toxin synthesis by RIP and RAP.

Ji et al. *Proc. Natl. Acad. Sci. USA* (1995) describes an octapeptide that acts as an agr-dependent autoinducer of RNAIII.

PCT publication no. WO 96/106579 by Novick et al. describes peptides having a molecular weight of less than 3 kDa capable of inhibiting agr-RNAIII transcription in *S. aureus*. In addition, PCT publication no. WO 97/44349 by Novick et al. describes cyclic peptides of between six to twelve amino acids, including cysteine from the 28 position of the agrD region as capable, in vitro, of inhibiting agr-RNAIII transcription in *S. aureus*.

Ji et al. *Science* 276:2027–30 (1997) describe the phenomenon of bacterial interference mediated by octapeptides.

Balaban et al. *Science* 280:438–440 (1998) describes inhibition of inhibit *S. aureus* infection in mice using RIP, synthetic peptides, and anti-RAP antibodies.

Novick et al. *Curr. Opin. Microbiol.* 2:40–5 (1999) reviews virulence gene regulation in staphylococci and other gram-positive bacteria.

Mayville et al. *Proc. Natl. Acad. Sci. USA* 96:1218–23 (1999) reports that the octapeptide contains a thiolactone moiety.

Sequence data from the genome of *S. aureas* and contig 876 were obtained from the Staphylococcus aureus Genome Sequencing Project website having an Internet address at www. genome.ou.edu/staph blast.html [at http://www.genome.ou.edu/staph_blast.html].

SUMMARY OF THE INVENTION

The present invention is directed to a protein isolated from *S. aureus* that is the target of RAP, called TRAP, which is characterized by a molecular weight of about 21 KDa, is capable of being phosphorylated by RAP, and comprises an amino acid sequence of SEQ ID NO:2. In addition, the present invention is directed towards an antibody immunoreactive with TRAP that is preferably a monoclonal antibody or a humanized antibody but may be a polyclonal antibody. The invention provides a method of treating *S. aureus* infection by administering such a TRAP-inhibiting agent. The invention also features methods for identifying compounds that inhibit TRAP activity and/or inhibit TRAP-RAP interaction.

In one aspect, the invention features an isolated TRAP polypeptide. In specific embodiments, the TRAP polypeptide comprises an amino acid sequence of SEQ ID NO:2.

An aspect of the invention is a pharmaceutical formulation for use in inhibiting or suppressing the production of toxins by a Staphylococcus bacteria, particularly *S. aureus*.

Another aspect of the invention is a formulation comprising a pharmaceutically acceptable carrier and a TRAP inhibitory agent, e.g., an anti-TRAP antibody.

Another aspect of the invention is a method of treating a Staphylococcus infection by administering a therapeutically effective amount of a formulation comprising a pharmaceutically acceptable carrier and a TRAP inhibitory agent, Still another aspect of the invention is a method for identifying agents that inhibit production of Staphylococcus virulence factors by screening agents for activity in inhibiting TRAP-RAP interaction and/or inhibiting activity of phosphorylated TRAP.

A feature of the invention is that the identification and isolation of TRAP provides a new target for use in screening of compounds for use in prevention and/or treatment of infection by *S. aureus*.

Another feature of the invention is that TRAP inhibitory agents, either alone or in different combinations with other compounds effective in inhibition production of virulence factors by *S. aureus* can be used to effectively treat Staphylococcus infections.

These and other objects, advantages, features and aspects of the present invention will become apparent to those skilled in the art upon reading this disclosure.

DETAILED DESCRIPTION OF THE PREFERRED EMBODIMENTS

Figure 1:
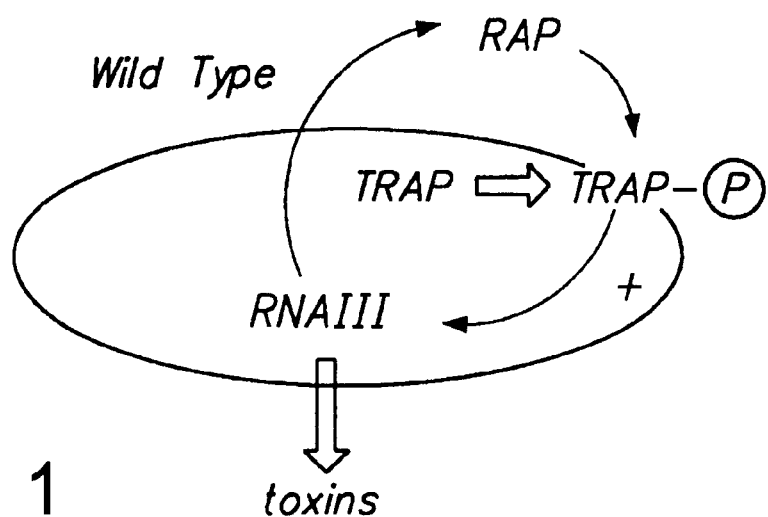
FIG. 1 is a simplified diagram summarizing the role of RAP, TRAP, and RNAIII and in the production of toxins in Staphylococcus.

Before the present proteins, formulations and methods are described, it is to be understood that this invention is not limited to the particular compounds, characteristics and steps described, as such may, of course, vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications and patents mentioned herein are incorporated herein by reference to disclose and describe the specific methods and/or materials in connection with which the publications and patents are cited.

The publications and patents discussed herein are provided solely for their disclosure prior to the filing date of the present application. Nothing herein is to be construed as an admission that the present invention is not entitled to antedate such publication or patent by virtue of prior invention. Further, the dates of publication or issuance provided may be different from the actual dates which may need to be independently confirmed.

Definitions

"TRAP" is meant to refer to a protein target of RAP and is an approximately 21 kDa polypeptide obtained from a Staphylococcus bacteria, preferably from *Staphylococcus aureus*, and which is phosphorylated by RAP, i.e., RNAIII activating protein. In one specific embodiment, TRAP comprises an amino acid sequence of SEQ ID NO:2. Unless specifically noted otherwise, "TRAP" as used herein is meant to encompass naturally-occurring TRAP protein, recombinant TRAP protein, full-length TRAP protein, and biologically active fragments thereof (e.g., a protein of TRAP that can be phosphorylated by RAP (e.g., for use in screening assays)).

"RAP" or "RNAIII activating protein" is meant to refer to an approximately 38 kDa protein obtained from a Staphylococcus bacteria, preferably from *Staphylococcus aureus*, which mediates phosphorylation of TRAP. Unless specifically noted otherwise, "RAP" as used herein is meant to encompass naturally-occurring RAP protein, recombinant RAP protein, full-length RAP protein, and biologically active fragments thereof (e.g., a fragment of RAP that is still active in phosphorylation of TRAP (and thus can be used in, for example, screening assays)).

"Optional" or "optionally" means that the subsequently described event or circumstance may or may not occur, and that the description includes instances where said event or circumstance occurs and instances in which it does not.

The term "treatment" or "treating" means any therapeutic intervention in a mammal, preferably a human or bovine, including:

(i) prevention, that is, causing the clinical symptoms not to develop, e.g., preventing infection from occurring and/or developing to a harmful state;

(ii) inhibition, that is, arresting the development of clinical symptoms, e.g., stopping an ongoing infection so that the infection is eliminated completely or to the degree that it is no longer harmful; and/or (iii) relief, that is, causing the regression of clinical symptoms, e.g., causing a relief of fever and/or inflammation caused by an infection.

Treatment is generally applied to any mammal susceptible to of having an *S. aureus* infection (e.g., mammals, birds, etc.), generally a mammal, usually a human or bovine where the treatment can be applied for prevention of bacterial infection of for amelioration of active bacterial infection, where the bacteria is a Staphylococcus bacteria, specifically *Staphylococcus aureus*.

The terms "effective amount" and/or "therapeutic amount" means a dosage sufficient to provide treatment for the disease state being treated. This will vary depending on the patient, the disease and the treatment being effected. In the case of a bacterial infection, an "effective amount" is that amount necessary to substantially improve the likelihood of treating the infection, in particular that amount which improves the likelihood of successfully preventing infection or eliminating infection when it has occurred.

The term "protein" as used herein is intended to encompass any amino acid sequence and include modified sequences (e.g., glycosylated, PEGylated, containing conservative amino acid substitutions, etc.). The term includes naturally occurring (e.g., non-recombinant) proteins, polypeptides, peptides, (particularly those isolated from a Staphylococcus bacteria, more particularly from *Staphylococcus aureus*), and oligopeptides, as well as those which are recombinantly or synthetically synthesized according to methods well known in the art. As used in connection with the present invention the term "protein" is specifically intended to cover naturally occurring proteins which occur in *Staphylococcus aureus* and useful in treating infection or in generating antibodies useful in treating infection. Where "polypeptide" or "protein" are recited herein to refer to an amino acid sequence of a naturally-occurring protein molecule, "polypeptide," "protein," and like terms are not meant to limit the amino acid sequence to the complete, native amino acid sequence associated with the recited protein molecule.

"Polynucleotide" as used herein refers to an oligonucleotide, nucleotide, and fragments or portions thereof, as well as to peptide nucleic acids (PNA), fragments, portions or antisense molecules thereof, and to DNA or RNA of genomic or synthetic origin which can be single- or double-stranded, and represent the sense or antisense strand. Where "polynucleotide" is used to refer to a specific polynucleotide sequence (e.g. a TRAP protein-encoding polynucleotide), "polynucleotide" is meant to encompass polynucleotides that encode a protein that is functionally equivalent to the recited protein, e.g., polynucleotides that are degenerate variants (i.e., variants in nucleic acid sequence that encode the same amino acid sequence and exist due to the degeneracy of the genetic code), or polynucleotides that encode biologically active variants or fragments of the recited protein.

By "antisense polynucleotide" is mean a polynucleotide having a nucleotide sequence complementary to a given polynucleotide sequence including polynucleotide sequences associated with the transcription or translation of the given polynucleotide sequence (e.g., a promoter) and/or to a coding sequence of the given polynucleotide sequence, where the antisense polynucleotide is capable of hybridizing to a polynucleotide sequence. Of particular interest are antisense polynucleotides capable of inhibiting transcription and/or translation, either in vitro or in vivo.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen et al 1993 Anticancer Drug Des 8:53–63).

The term "antibody" is meant to refer to an immunoglobulin protein which is capable of binding an antigen. Antibody as used herein is meant to include the entire antibody as well as any antibody fragments (e.g., F(ab)', Fab, Fv) capable of binding the epitope, antigen or antigenic fragment of interest. Preferred antibodies for assays and vaccines of the invention are immunoreactive or immunospecific for and therefore specifically and selectively bind to a protein of interest, e.g., an anti-TRAP antibody. The term "antibody" encompasses all types of antibodies, e.g., polyclonal, monoclonal, humanized, chimeric, and those produced by the phage display methodology. Particularly preferred antibodies of the invention are antibodies which have a relatively high degree of affinity for TRAP. An antibody of the invention is preferably immunoreactive with and immunospecific for a specific species, e.g., TRAP obtained from *Staphylococcus aureus*.

As used herein the term "isolated" is meant to describe a compound of interest (e.g., either a polynucleotide or a polypeptide) that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound (e.g., either a polynucleotide or a polypeptide) that is removed from its natural environment and is at least 60% free, preferably 75% free, and most preferably 90% free from other components with which it is naturally associated.

"Antigenic fragment" of a protein is meant a portion of such a protein which is capable of binding an antibody.

By "binds specifically" is meant high avidity and/or high affinity binding of an antibody to a specific polypeptide, e.g., epitope of a protein, e.g., TRAP protein. Antibody binding to its epitope on this specific polypeptide is preferably stronger than binding of the same antibody to any other epitope, particularly those which may be present in molecules in association with, or in the same sample, as the specific polypeptide of interest, e.g., binds more strongly to epitope fragments of a protein such as TRAP so that by adjusting binding conditions the antibody binds almost exclusively to an epitope site or fragments of a desired protein.

By "detectably labeled antibody" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels known in the art include radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies are well known in the art (see, for example, Harlow and Lane, eds. (Antibodies: A Laboratory Manual (1988) Cold Spring Harbor Laboratory Press, Cold Spring Harbor, N.Y.)). Europium is a useful label.

Overview of the Invention

Figure 2:
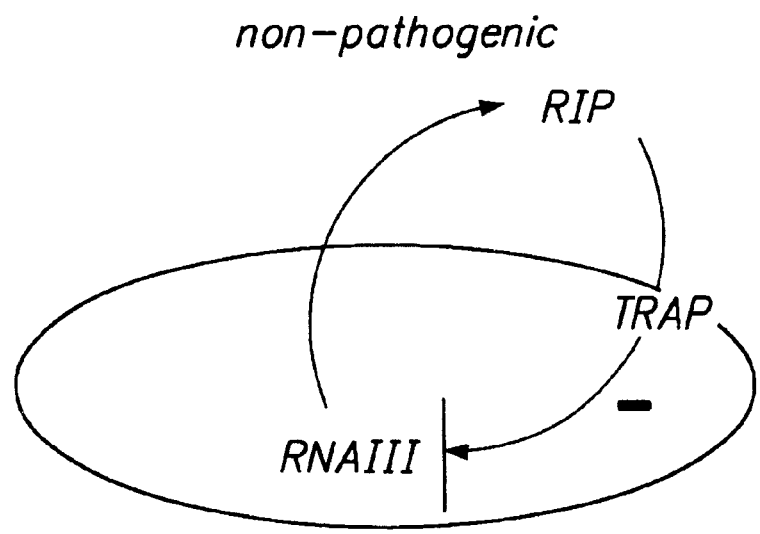
FIG. 2 is a simplified diagram summarizing the role of RIP and inhibition of virulence factor production in non-pathogenic Staphylococcus.

The present invention is based on the discovery and isolation of the target of RAP, termed TRAP. TRAP, an approximately 21 kDa protein, is specifically phosphorylated by RAP; RIP inhibits its TRAP phosphorylation. Phosphorylation of TRAP leads to induction of RNAIII, which in turn leads to the expression of *S. aureus* virulence factors. Thus, in the presence of RAP, TRAP is phosphorylated, RNAIII induced, and virulence factors secreted by *S. aureus* (FIG. 1). In the presence of RIP, RAP phosphorylation of TRAP is inhibited, and thus virulence factor production does not occur to a substantial or detectable level (FIG. 2).

According to the discovery upon which the present invention is based, blocking of one or more site(s) on TRAP that are important in either interaction with RAP, phosphorylation of TRAP by RAP, and/or activity of TRAP in facilitating RNAIII transcription can disrupt the pathway by which toxins are formed by *S. aureus*. Furthermore, enhancing RIP activity, which is associated with TRAP-RAP inhibition, can also serve to disrupt the virulence factor production pathway in *S. aureus*. Thus, the present invention also features methods for identifying agents that inhibit or repress the induction of RNAIII by blocking TRAP activity (e.g., anti-TRAP antibodies), blocking RAP phosphorylation of TRAP (e.g., anti-RAP antibodies), and/or enhancing RIP-mediated TRAP inhibition, as well as agents so identified. Thus, the invention also encompasses vaccines and drug therapies to prevent and/or retard infections in humans and animals, particularly dairy animals, as an alternative to treatment with antibiotics.

Experiments described here demonstrate the isolation and characterization of TRAP or "target of RAP". *S. aureus* virulence factor production can be blocked by inhibiting TRAP activity in facilitating RNAIII production. TRAP activity can be inhibited by, for example, 1) inhibiting RAP activity in phosphorylation of TRAP, 2) enhancing RIP activity in blocking RAP phosphorylation, and/or 3) inhibiting activity of phosphorylated TRAP in inducing RNAIII production. Inhibiting TRAP activity can be accomplished by administering an agent that inhibits TRAP activity through one or more of these mechanisms. Accordingly, the invention encompasses methods for identifying such agents as well as methods of prevention and/or treatment of Staphylococcus infections by administration of such agents. A TRAP inhibitory agent (e.g., an anti-TRAP antibody) of or identified by the methods of the invention can be co-administered with other agents that have been identified as having activity in inhibiting *S. aureus* virulence factor production (e.g., with RIP derived from a non-pathogenic Staphylococcus)

The invention is described in more detail below.

TRAP Nucleic Acid and Proteins

The present invention provides a protein (TRAP) isolated and purified from *S. aureus* that is the target of RNAIII activating protein. The TRAP protein has a molecular weight of about 21 kDa and is phosphorylated by RNAIII activating proteins (RAP). The phosphorylation of TRAP reaches a peak at about the mid exponential phase of cell growth and TRAP is essentially dephosphorylated by the late log phase of cell growth. In one embodiment, TRAP is the protein encoded by a polynucleotide comprising the sequence of SEQ ID NO:1, and comprising an amino acid sequence of SEQ ID NO:2. These sequences are provided in the Sequence Listing below.

TRAP Nucleic Acid

The term "TRAP gene" is used generically to designate TRAP genes and their alternate forms. "TRAP gene" is also intended to mean the open reading frame encoding specific TRAP proteins, and adjacent 5' and 3' non-coding nucleotide sequences involved in the regulation of expression (e.g., promoter region). The gene may be introduced into an appropriate vector for extrachromosomal maintenance or for integration into the host. In one embodiment the TRAP gene comprises the sequence of SEQ ID NO:1.

TRAP regulatory sequences may be used to identify cis acting sequences required for transcriptional or translational regulation of TRAP expression, especially at different stages of growth (e.g., early, mid, and late log phase), and to identify cis acting sequences and trans acting factors that regulate or mediate TRAP expression. Such transcriptional or translational control regions may be operably linked to a TRAP coding sequence or other coding sequence. In one embodiment, the TRAP gene is provided as SEQ ID NO:1. In another embodiment, the TRAP coding sequence comprises nucleotide residues 63–565 of SEQ ID NO:1 where nucleotide residues 563–565 represent a stop codon. In one embodiment, the TRAP 5' untranslated region comprises nucleotide residues 1–62 of SEQ ID NO:1. A TRAP promoter region can be provided by nucleotide residues 1–40 of SEQ ID NO:1.

The nucleic acid compositions used in the subject invention may encode all or a part of the TRAP protein as appropriate. Fragments may be obtained of the DNA sequence by chemically synthesizing oligonucleotides in accordance with conventional methods, by restriction enzyme digestion, by PCR amplification, etc. For the most part, DNA fragments will be of at least about ten contiguous nucleotides, usually at least about 15 nt, more usually at least about 18 nt to about 20 nt, more usually at least about 25 nt to about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The TRAP gene and TRAP coding sequence are isolated and obtained in substantial purity, generally as other than an intact bacterial chromosome. Usually, the DNA will be obtained substantially free of other nucleic acid sequences that do not include a TRAP sequence or fragment thereof, generally being at least about 50%, usually at least about 90% pure and are typically "recombinant", i.e. flanked by one or more nucleotides with which it is not normally associated on a naturally occurring chromosome.

The DNA sequences are used in a variety of ways. They may be used as probes for identifying TRAP coding sequences of other strains of Staphylococcus or of other bacteria. Homologs isolated from other stains, species, or genera generally have substantial sequence similarity to one another, i.e. at least 75%, usually at least 90%, more usually at least 95% sequence identity. In general, TRAP-encoding sequences of the invention (including homologs, variants, etc.) are characterized by having a sequence identity greater than at least about 65%, preferably at least about 75%, more preferably at least about 85%, and can be greater than at least about 90% or more as determined by the Smith-Waterman homology search algorithm as implemented in MPSRCH program (Oxford Molecular). For the purposes of this invention, a sequence identity is calculated using the Smith-Waterman algorithm as follows: Global DNA sequence identity must be greater than 65% as determined by the Smith-Waterman homology search algorithm as implemented in MPSRCH program (Oxford Molecular) using an affine gap search with the following search parameters: gap open penalty, 12; and gap extension penalty, 1.

Nucleic acids having sequence similarity can also be detected by hybridization under low stringency conditions, for example, at 50° C. and 6×SSC (0.9 M saline/0.09 M sodium citrate) and remain bound when subjected to washing at 55° C. in 1×SSC (0.15 M sodium chloride/0.015 M sodium citrate). In addition, sequence identity may also be determined by hybridization under high stringency conditions, for example, at 50° C. or higher and 0.1×SSC (15 mM saline/0.15 mM sodium citrate). By using probes, particularly labeled probes of DNA sequences, one can isolate homologous or related genes. It may also be possible to identify homologs of TRAP from mammalian sources.

The TRAP-encoding DNA may also be used to detect expression of the gene in a biological specimen. Methods and materials for probing a sample for the presence of particular nucleotide sequences are well established in the literature and do not require elaboration here. mRNA is isolated from a cell sample. mRNA may be amplified by RT-PCR, using reverse transcriptase to form a complementary DNA strand, followed by polymerase chain reaction amplification using primers specific for the subject DNA sequences. Alternatively, mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to an TRAP sequence is indicative of TRAP gene expression in the sample.

The TRAP nucleic acid sequence may be modified for a number of purposes, particularly where they will be used intracellularly, for example, by being joined to a nucleic acid cleaving agent, e.g. a chelated metal ion, such as iron or chromium for cleavage of the gene; or the like.

The TRAP coding sequence and/or promoter sequence may be mutated in various ways known in the art to generate targeted changes in promoter strength, sequence of the encoded protein, etc. The DNA sequence or product of such a mutation will be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain. Other modifications of interest include production of fusion proteins (e.g., with green fluorescent proteins (GFP), luciferase, and the like).

Techniques for in vitro mutagenesis of cloned genes are known. Examples of protocols for scanning mutations may be found in Gustin et al., 1993 Biotechniques 14:22; Barany, 1985 Gene 37:111–23; Colicelli et al., 1985 Mol Gen Genet 199:537–9; and Prentki et al., 1984 Gene 29:303–13. Methods for site specific mutagenesis can be found in Sambrook et al., 1989 Molecular Cloning: A Laboratory Manual, CSH Press, pp. 15.3–15.108; Weiner et al., 1993 Gene 126:35–41; Sayers et al., 1992 Biotechniques 13:592–6; Jones and Winistorfer, 1992 Biotechniques 12:528–30; Barton et al., 1990 Nucleic Acids Res 18:7349–55; Marotti and Tomich, 1989 Gene Anal Tech 6:67–70; and Zhu 1989 Anal Biochem 177:120–4.

TRAP Protein

TRAP protein can be produced by any suitable means, e.g., by isolated from a bacteria that naturally expresses TRAP, by recombinant means (e.g., by expression of a polynucleotide having a sequence of SEQ ID NO:1), by synthetic means, and the like.

In one embodiment, TRAP is isolated directly from a strain of Staphylococcus producing TRAP, e.g., S. aureus. Typically, wild type cells are collected at exponential culture (OD read as 0.3 at 300 nm). The collected cells are centrifuged and the media exchanged to PFB to remove $^{32}$P. Cells are then resuspended in water, sonicated, centrifuged to remove non-soluble material, and soluble material applied to an HPLC gel filtration column. Positive fraction (determined by peak radioactivity and confirmed by separating a sample on SDS PAGE) is applied to an HPLC anion exchange column and positive fraction collected.

The staphylococci bacterium from which TRAP may be isolated may include, but is not limited to, S. aureus, S. capitus, S. warneri, S. capitis, S. caprae, S. carnosus, S. saprophyticus, S. chronii, S. simulans, S. caseolyticus, S. epidermidis, S. haemolyticus, S. hominis, S. hyicus, S. kloosii, S. lentus, S. lugdunensis, S. scruri, S. simulans, and S. xylosus.

In another embodiment, TRAP-encoding nucleic acid is employed to synthesize full-length TRAP protein or fragments thereof, particularly fragments corresponding to functional domains (e.g., phosphorylation sites that interact with RAP, etc.); and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

The polypeptides may be expressed in prokaryotes or eukaryotes in accordance with conventional ways, depending upon the purpose for expression. For large scale production of the protein, a unicellular organism, such as E. coli, B. subtilis, S. cerevisiae, or cells of a higher organism such as vertebrates, particularly mammals, e.g. COS 7 cells, may be used as the expression host cells. Alternatively, TRAP fragments can be synthesized.

With the availability of the polypeptides in large amounts, by employing an expression host, TRAP protein can be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure.

The TRAP proteins can be used for the production of antibodies, where short fragments provide for antibodies specific for the particular polypeptide, and larger fragments or the entire protein allow for the production of antibodies over the surface of the polypeptide. Antibodies may be raised to the wild-type or variant forms of TRAP. Antibodies may be raised to isolated peptides corresponding to these domains, or to the native protein, e.g. by immunization with cells expressing TRAP, immunization with liposomes having TRAP protein inserted in the membrane, etc.

Anti-TRAP antibodies

The present invention also provides an antibody that specifically binds and is immunoreactive with TRAP. The antibody may be monoclonal, polyclonal or humanized, and is prepared using methods well known in the art. In general, antibodies are prepared in accordance with conventional ways, where the protein or an antigenic portion thereof is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. In a preferred embodiment, the spleen or lymph node cells and myeloma cells are mixed in about 20:1 to about 1:1 ratio, but preferably in about 2:1 ratio. It is preferred that the same species of animal serve as the source of somatic and myeloma cells used in the fusion procedure, where the animal is chosen from rat, mouse, rabbit, cow, chicken, turkey, or man. The fusion of the somatic and myeloma cells produces a hybridoma, which is grown in culture to produce the desired monoclonal antibody by standard procedures. For further description, see, for example, Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in E. coli, and the heavy and light chains mixed to further enhance the affinity of the antibody. Alternatives to in vivo immunization as a method of raising antibodies include binding to phage "display" libraries, usually in conjunction with in vitro affinity maturation.

The polyclonal antibodies of the present invention may be produced by injecting a rat, a mouse, a rabbit, a cow, a chicken, or a turkey with TRAP to initiate an immunogenic response. TRAP may be coupled to a protein carrier such as deyhole limpet hemocyanin (KLH) or bovine serum albumin (BSA). An adjuvant may also be used. After a suitable amount of time to establish a high-titer of anti-TRAP antibodies, the serum or eggs are collected. The presence of antibody in the serum or eggs may be tested by radioimmunoassay (RIA), by enzyme-linked immunosorbent assay (ELISA), or by immunoprecipitation. The immunoglobulins may be isolated by the sequential precipitation methods, by conventional methods of "salting out" the protein fractions from a salt solution, or by chromatographical methods well known to those skilled in the art.

Identifying Agents Suitable for Treating Staphylococcus Infection

Of particular interest in the present invention is the identification of agents that have activity in affecting the expression and/or function of TRAP. In general agents of interest are those that 1) inhibit TRAP activity, e.g., by inhibiting the ability of unphosphorylated TRAP to become phosphorylated by RAP, or by inhibiting the ability of phosphorylated TRAP to facilitate production of RNAIII);

2) inhibit activity of RAP in interaction with and/or phosphorylation of TRAP; and/or 3) enhancing or mimicking RIP activity in inhibition of TRAP. Such agents are candidates for development of treatments for infection of pathogenic Staphylococcus. Of particular interest are screening assays for agents that have a low toxicity for human cells and/or high specificity for Staphylococcus, preferably with substantially no or little pressure for selection of strains resistant to the action of the agent, and without substantially affecting normal flora of the host (e.g., as distinguished from wide-spectrum antibiotics).

The term "agent" as used herein describes any molecule, e.g. protein or pharmaceutical, with the capability of altering TRAP activity, or mimicking or enhancing RIP activity, as described above. Generally a plurality of assay mixtures are run in parallel with different agent concentrations to detect differential responses to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, pheromones, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial (e.g., non-pathogenic Staphylococcus), fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Screening of Candidate Agents

A wide variety of in vitro assays may be used to screen candidate agents, including labeled in vitro binding assays, e.g., protein-protein binding, protein-DNA binding assays, electrophoretic mobility shift assays, immunoassays for protein binding, and the like. Purified naturally-occurring or recombinant TRAP, RAP, and RIP proteins, and/or synthetically produced peptides or fragments of TRAP, RAP, and/or RIP, can be used in various screening assays to identify ligands or substrates that bind to, modulate (e.g., increase or inhibit), or mimic the action of the native proteins. The purified proteins may also be used for determination of three-dimensional crystal structure, which can be used for modeling intermolecular interactions, transcriptional regulation, etc.

The screening assay can be a binding assay, wherein one or more of the molecules may be joined to a label, and the label directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures. In general, the particular type of screening assay employed will preferably one amenable to parallel, simultaneous screening of a large number of candidate agents.

Because TRAP, RAP, and RIP are involved in a signal transduction pathway that involves activity in (RAP) or inhibition of (RIP) phosphorylation of TRAP, one screening assay of particular interest involves detection of TRAP phosphorylation. TRAP phosphorylation screening assays may be performed in, for example, a cell-free assay (e.g., with substantially purified proteins), in whole cell assays (e.g., using whole Staphylococcus or recombinant host cells expressing TRAP, RAP, and/or RIP). Phosphorylation screening assays may be performed in a variety of ways. For example, the candidate agent may be combined with detectably labeled phosphate, TRAP, and varying concentrations of RAP to determine if the candidate agent competes with RAP to inhibit TRAP phosphorylation by RAP. Alternatively, the candidate agent may be combined with detectably labeled phosphate, RAP, TRAP, and varying concentrations of RIP to determine if the candidate agent mimics RIP activity. Assays, and methods for performing such assays, that can be used in the screening assay of the invention are well known in the art. See, for example, Roychoudhury et al. *Proc. Natl. Acad. Sci. U.S.A.*, 90: 965–969 (1993), which describes identification of compounds that block the expression of alginate, a virulence factor for the cystic fibrosis pathogen *Pseudomonas aeruginosa*, and which reference is incorporated herein by reference with respect to drug screening assays and methods and compositions for performing same.

Screening assays of the present invention also encompass assays that examine the effect of candidate agents on the roles of TRAP, RAP, and RIP in RNAIII production and/or virulence factor production. For example, the candidate agent may be contacted with pathogenic Staphylococcus and the levels of TRAP phosphorylation and/or rnaiii transcription in the presence of the agent compared to TRAP phosphorylation and/or rnaiii transcription levels in the presence of RIP, RAP, and/or a combination of RIP and RAP. Such screening assays can utilize recombinant host cells containing reporter gene systems such as CAT (chloramphenicol acetyltransferase), β-galactosidase, and the like operably associated with rnaiii or virulence factor genes to facilitate detection of rnaiii or virulence gene transcription or to facilitate detection of RNAIII or virulence factor production. Alternatively, the screening assay can detect rnaiii or virulence factor transcription using hybridization techniques (e.g., Northern blot, PCR, etc.) well known in the art.

A variety of other reagents may be included in the screening assays described herein. Where the assay is a binding assay, these include reagents like salts, neutral proteins, e.g. albumin, detergents, etc. that are used to facilitate optimal protein-protein binding, protein-DNA binding, and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hours will be sufficient.

Screening of Candidate Agents in an Animal Model

Agents having a desired activity as determined in the assays described above can be further screened for their ability to affect Staphylococcus virulence factor production, and to affect Staphylococcus infection, in a non-human animal model. The animal model selected will vary with a number of factors including, but not limited to, the particular pathogenic strain of Staphylococcus against which candidate agents are to be screened, the ultimate host for which the candidate agents are to serve as therapeutics, etc. Animals suitable for use in screening assays include any animal susceptible to infection by the selected Staphylococcus species. For example, where the Staphylococcus species is S. aureus, the animal model can be a rodent model, preferably a mouse model.

In general, the candidate agent is administered to a non-human animal susceptible to Staphylococcus infection, where the animal has been previously infected with Staphylococcus or receives an infectious does of Staphylococcus in conjunction with the candidate agent. Preferably, the animal has no detectable RAP antibodies. The candidate agent can be administered in any manner desired and/or appropriate for delivery of the agent in order to effect a desired result. For example, the candidate agent can be administered by injection (e.g., by injection intravenously, intramuscularly, subcutaneously, or directly into the tissue in which the desired affect is to be achieved), topically, orally, or by any other desirable means. Normally, this screen will involve a number of animals receiving varying amounts and concentrations of the candidate agent (from no agent to an amount of agent hat approaches an upper limit of the amount that can be delivered successfully to the animal), and may include delivery of the agent in different formulations. The agents can be administered singly or can be combined in combinations of two or more, especially where administration of a combination of agents may result in a synergistic effect.

The effect of agent administration upon the animal model can be monitored by any suitable method, such as assessing the number and size of Staphylococcus-associated lesions, overall health, etc. Where the candidate agent affects Staphylococcus infection in a desirable manner (e.g., by reducing infectious load, facilitating lesion regression, etc.), the candidate agent is identified as an agent suitable for use in treatment of Staphylococcus infection.

Identified Candidate Agents

The compounds having the desired pharmacological activity may be administered in a physiologically acceptable carrier to a host for treatment of pathogenic Staphylococcus infection. The therapeutic agents may be administered in a variety of ways, orally, topically, parenterally e.g. subcutaneously, intraperitoneally, intravascularly, intrapulmonary (inhalation), etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Treating Staphylococcus Infection

The invention provides a method for preventing or treating a human or an animal susceptible to infection by a pathogenic Staphylococcus (e.g., S. aureus in humans) by administering an agent that inhibits TRAP activity in facilitating virulence factor production, e.g., by inhibition phosphorylation or TRAP and/or by inhibiting activity of phosphorylated TRAP in mediating expression of RNAIII and subsequent virulence factor production.

In one embodiment, the host is treated by administration of a TRAP inhibitor, such as am anti-TRAP antibody. In one embodiment the TRAP inhibitor is co-administered with other TRAP inhibitors and/or co-administered with other inhibitors of S. aureus virulence factor production, e.g., co-administered with RIP. In another embodiment a TRAP inhibitor, RIP, and a RAP inhibitor (e.g., an anti-RAP antibody) are administered. Such combination therapies (e.g., administration of multiple TRAP inhibitory agents; administration of TRAP and RIP; and/or administration of TRAP inhibitor, RIP, and/or RAP inhibitor) may involve co-administration or sequential administration of the active components. The dosage regimen may be adjusted to provide the optimum therapeutic response. For example, several divided doses may be administered daily or the dose may be proportionally reduced as indicated by the therapeutic situation. The active compounds may be administered in any convenient manner, such as by oral, intravenous, intramuscular, subcutaneous, buccal, transdermal, or inhalation routes.

Formulations composed of RIP, TRAP inhibitor and/or RAP inhibitor are administered at a therapeutically effective dosage, e.g., a dosage sufficient to improve the chance of successful prevention or treatment of infection. Administration of such a formulation can be via any of the accepted modes of administration for agents that serve similar utilities, preferably by systemic administration.

Human dosage levels for treating infections are known and generally include a daily dose from about 0.1 to 500.0 mg/kg of body weight per day, preferably about 6.0 to 200.0 mg/kg, and most preferably about 12.0 to 100.0 mg/kg. Generally, it is sought to obtain a serum concentration of such a formulation approximating or greater than circulating levels needed to reduce or eliminate any infection in less than 10 days. For administration to a 70 kg person, the dosage range would be about 50 mg to 3.5 g per day, preferably about 100 mg to 2 g per day, and most preferably about 200 mg to 1 g per day. The amount of formulation administered will, of course, be dependent on the subject and the severity of the affliction, the manner and schedule of administration and the judgment of the prescribing physician.

In employing formulation for treatment of infections, any pharmaceutically acceptable mode of administration can be used. The formulations can be administered either alone or in combination with other pharmaceutically acceptable excipients, including solid, semi-solid, liquid or aerosol dosage forms, such as, for example, tablets, capsules, powders, liquids, gels, suspensions, suppositories, aerosols or the like. The formulations can also be administered in sustained or controlled release dosage forms (e.g., employing a slow release bioerodable delivery system), including depot injections, osmotic pumps (such as the Alzet implant made by Alza), pills, transdermal and transcutaneous (including electrotransport) patches, and the like, for prolonged administration of a predetermined rate, preferably in unit dosage forms suitable for single administration of precise dosages. The compositions will typically include a conventional pharmaceutical carrier or excipient and a formulation of the invention. In addition, these compositions may include other active agents, carriers, adjuvants, etc. Generally, depending on the intended mode of administration, the pharmaceutically acceptable composition will contain about 0.1% to 90%, preferably about 0.5% to 50%, by weight of active compound, the remainder being suitable pharmaceutical excipients, carriers, etc. Actual methods of preparing such dosage forms are known, or will be apparent, to those skilled in this art. For example, see *Remington's Pharmaceutical Sciences,* Mack Publishing Company, Easton, Pa., 15th Edition, 1975.

Parental administration is generally characterized by injection, either subcutaneously, intradermally, intramuscularly, or intravenously, preferably subcutaneously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, and the like.

The percentage of active ingredient contained in such parental compositions is highly dependent on the specific nature thereof, as well as the needs of the subject. However, percentages of active ingredient of 0.01% to 10% in solution are employable, and will be higher if the composition is a solid which will be subsequently diluted to the above percentages. Preferably, the composition will comprise 0.2–2% of the active ingredient in solution.

A more recently devised approach for parental administration employs the implantation of a slow-release or sustained-release system, such that a constant level of dosage is maintained. Various matrices (e.g., polymers, hydrophilic gels, and the like) for controlling the sustained release, and for progressively diminishing the rate of release of active agents are known in the art. See U.S. Pat. No. 3,845,770 (describing elementary osmotic pumps); U.S. Pat. Nos. 3,995,651, 4,034,756 and 4,111,202 (describing miniature osmotic pumps); U.S. Pat. Nos. 4,320,759 and 4,449,983 (describing multichamber osmotic systems referred to as push-pull and push-melt osmotic pumps); and U.S. Pat. No. 5,023,088 (describing osmotic pumps patterned for the sequentially timed dispensing of various dosage units).

Formulations of active components may also be administered to the respiratory tract as a nasal or pulmonary inhalation aerosol or solution for a nebulizer, or as a microfine powder for inhalation, alone or in combination with an inert carrier such as lactose, or with other pharmaceutically acceptable excipients. In such a case, the particles of the formulation may advantageously have diameters of less than 50 microns, preferably less than 10 microns. See, e.g., U.S. Pat. No. 5,364,838, which discloses a method of administration for insulin that can be adapted for the administration of formulations of the present invention.

Vaccination

The invention provides a vaccine for inoculating a human or a animal susceptible to infection by a pathogenic Staphylococcus (e.g., *S. aureus*) by administering TRAP, or an antigenically effective portion of TRAP, in a pharmaceutically acceptable carrier, which may optionally comprise an adjuvant. Formulations appropriate for elicitation of the immune response are well known in the art. In general, the host is exposed to the antigen, such as TRAP, which perturbs the host's immune system and results in an immune response towards the antigen. An adjuvant can be added with the antigen to increase the immune response to the antigen. The amount of polypeptide administered is an amount sufficient to elicit a protective immune response in the host. Methods for determining such appropriate amounts are routine and well known in the art. For example, TRAP and/or antigenically effective portion(s) thereof can be used to vaccinate an animal model of Staphylococcus infection. The amounts effective in such animal models can be extrapolated to other hosts (e.g., livestock, humans, etc.) in order to provide for an amount effective for vaccination.

Coated Devices

The invention provides for a device, the surface of which is coated with a composition having an amount of A TRAP inhibitory agent (e.g., an anti-TRAP antibody) effective to inhibit production of virulence factors by pathogenic Staphylococcus. The coated device may be any device which may be associated with a risk of Staphylococcus infection or exposure of a host (e.g., surgery patient, menstruating female, etc.) to Staphylococcus virulence factors.

Coated devices encompassed by the present invention include, but are not limited to, catheters, needles, surgical instruments (e.g., scalpels, sponges, retractors, etc.), bandages and bandage materials (e.g., gauze, dressings, etc.), artificial joints, heart valves, and tampons. Such devices have a tendency to bring Staphylococci into contact with the host, or to attract colonizations by staph bacteria (e.g., tampons). In such situations, the coated devices may prevent or reduce Staphylococcus infection, or prevent or reduce the development of serious symptoms associated with exposure to Staphylococcus virulence factors.

EXAMPLES

The following examples are put forth so as to provide those of ordinary skill in the art with a complete disclosure and description of how to make and use the present invention and are not intended to limit the scope of what the inventors regard as their invention nor are they intended to represent or imply that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Purification of TRAP

Typically, wild type cells are collected at exponential culture (OD read as 0.3 at 300 nm). Centrifuged and their media exchanged to PFB (phosphate free buffer). RAP and $P^{32}$ are added, cells are continued to grow for an additional hour at 37° C. with shaking, cells collected and washed in PBS to remove $P^{32}$. Cells are then resuspended in water, sonicated, centrifuged to remove non soluble material, and soluble material applied to an HPLC gel filtration column in 0.1× PBS. Positive fraction (determined by peak radioactivity and confirmed by separating a sample on SDS PAGE) is applied to an HPLC anion exchange column in 0.1× PBS. Proteins are eluted by a 0–1 M NaCl gradient in 0.1× PBS and positive fraction collected (usually eluted at about 0.75 M NaCl).

Example 2

Phosphorylation of TRAP by RAP

Figure 3:
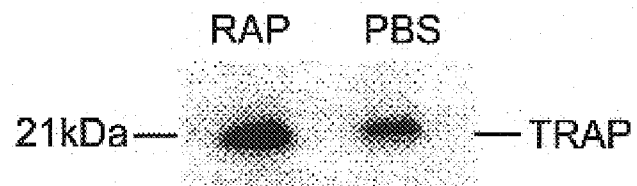
FIG. 3 is an autoradiogram of *S. aureus* cells incubated in phosphate free buffer (PFB) with $^{32}$P with RAP in PBS (left column) and with PBS alone (right column) as a control showing that TRAP is an approximately 21 kDa protein specifically phosphorylated by RAP. The incubated cells were collected, applied to SDS PAGE, and gel autoradiographed to obtain an autoradiogram.
Figure 4:
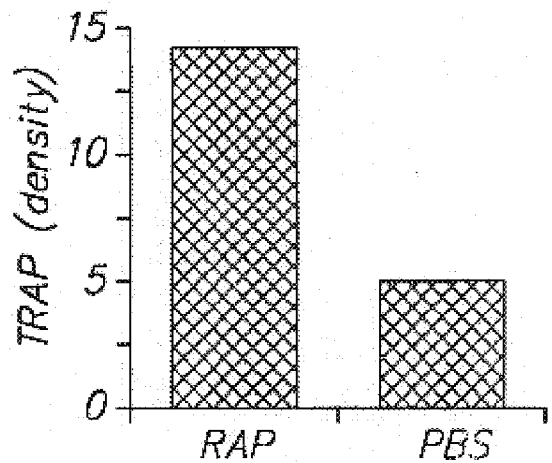
FIG. 4 is a bar graph obtained by scanning the density of the bands of FIG. 3.

In vivo phosphorylation assays were carried out using the protein isolated in Example 1. Wild type early exponential *S. aureus* cells were incubated for 1 hr in phosphate free buffer (PFB) together with $^{32}P$, with RAP (in PBS) or with PBS only as a control. The RAP used in the assay was obtained as described in Balaban et al., *Science* 280:438–440 (1998). Cells were collected, applied to SDS PAGE, and the gel autoradiographed. The autoradiogram was scanned and the density of the bands determined. The results, provided in FIGS. 3 and 4, show that RAP causes the specific phosphorylation of the 21 kDa protein.

In order to determine whether RAP induces synthesis of TRAP as well as its phosphorylation, the in vivo phosphorylation assay described above were repeated in the presence of 100 µg/ml chloramphenicol (Cm), and inhibitor of protein synthesis. The results of these experiments (not shown) indicated that RAP activates TRAP phosphorylation in the presence of Cm, suggesting that RAP activates TRAP phosphorylation and not TRAP synthesis.

Figure 5:
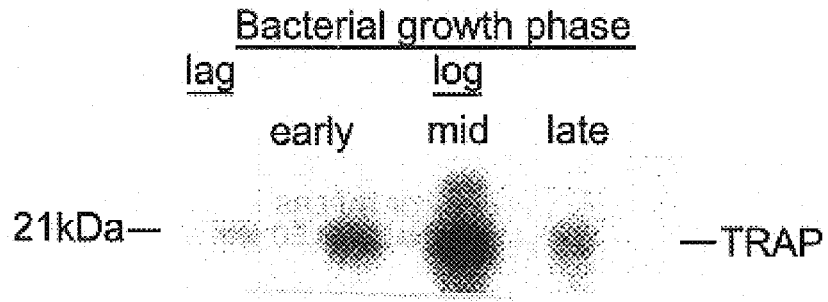
FIG. 5 is an autoradiogram of *S. aureus* cells grown from lag phase to late log phase of growth in PFB with $^{32}$P. The cells were collected, applied to SDS PAGE and the gel autoradiographed.
Figure 6:
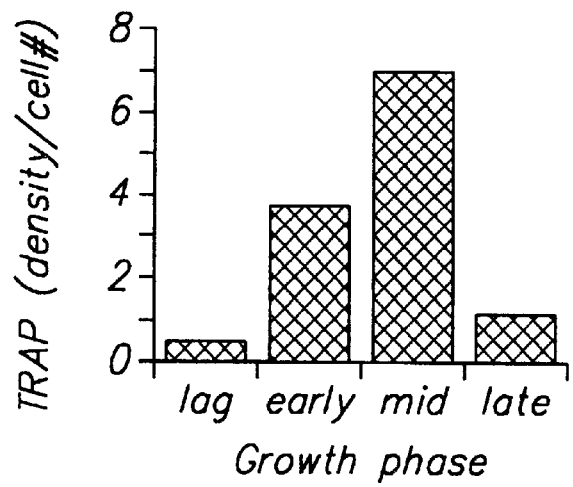
FIG. 6 is a bar graph obtained by scanning the bands of FIG. 5 to determine their density.
Figure 7:
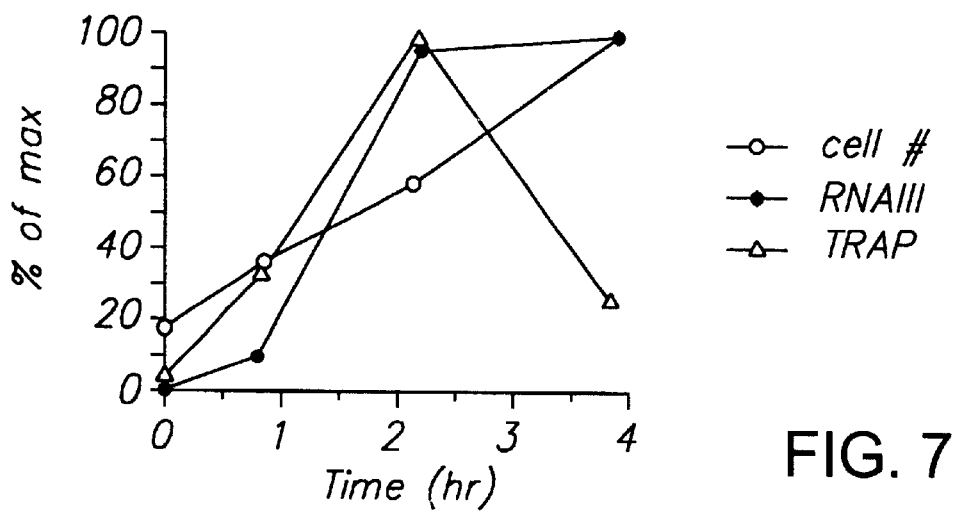
FIG. 7 is a graph of the amounts of TRAP, RNAIII, and cell number over time in hours.

To determine at what stage(s) during bacterial growth that are associated with RAP phosphorylation of TRAP, wild type *S. aureus* were grown from lag phase to late log phase of growth in the present of $^{32}P$. Cells were collected applied to SDS PAGE, and the gel autoradiographed, or the amount of RNAIII determined as described (Balaban et al. *Proc. Natl. Acad. Sci. U.S.A.* 92:1619–1623 (1995)). The results in FIGS. 5–7 show that peak phosphorylation of TRAP was reached at the mid-exponential phase of growth and TRAP is dephosphorylated by late log phase of growth.

Example 3

TRAP is not Encoded or Regulated by agr

Figure 8:
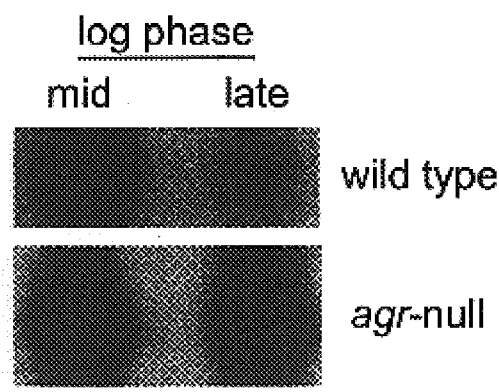
FIG. 8 is an autoradiogram showing TRAP phosphorylation in mutant agr-null *S. aureus* cells.

In order to determine whether TRAP phosphorylation is dependent on agr, wild type and an agr-null strain RN6911 of *S. aureus* were grown from lag phase to late log phase in PFB together with $^{32}P$ RN6911 is a mutant strain that contains a tetM gene in place of or within agr (Novick et al. *EMBO J.* 12:3967–75 (1993)). 2×10$^7$ cells were collected at each of mid and late log phases, applied to SDS PAGE, and the gel autoradiographed. Since TRAP was phosphorylated in both the wild type and agr-null strain (FIG. 8), TRAP phosphorylation is agr-independent. Like in wild type, peak phosphorylation in the agr-null strain is reached at the mid exponential phase of growth. However, unlike in the wild type strain, TRAP was not dephosphorylated by late log phase, suggesting that the agr itself, once activated in the mid exponential phase, produces a factor that downregulates TRAP phosphorylation.

Example 4

TRAP Phosphorylation Is Inhibited by an Octapeptide of agrD

Figure 9:
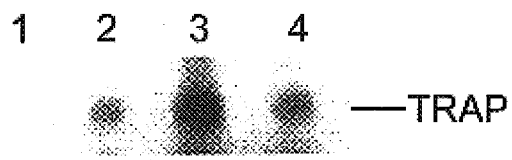
FIG. 9 is an autoradiograph showing the inhibition of TRAP phosphorylation by an octapeptide from agrD. Lane 1: flowthrough of wild type *S. aureus* post-exponential supernatants containing the octapeptide encoded by agrD (<3); lane 2: post-exponential supernatants of wild type *S. aureus* (total); lane 3: RAP; lane 4: PBS.
Figure 10:
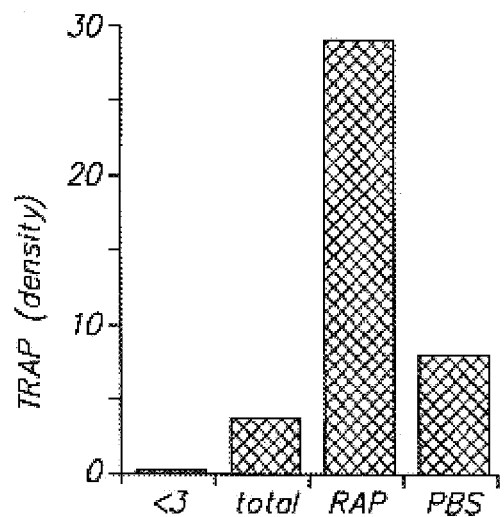
FIG. 10 is a bar graph showing the density of the of the bands on the autoradiogram of FIG. 9.
Figure 11:
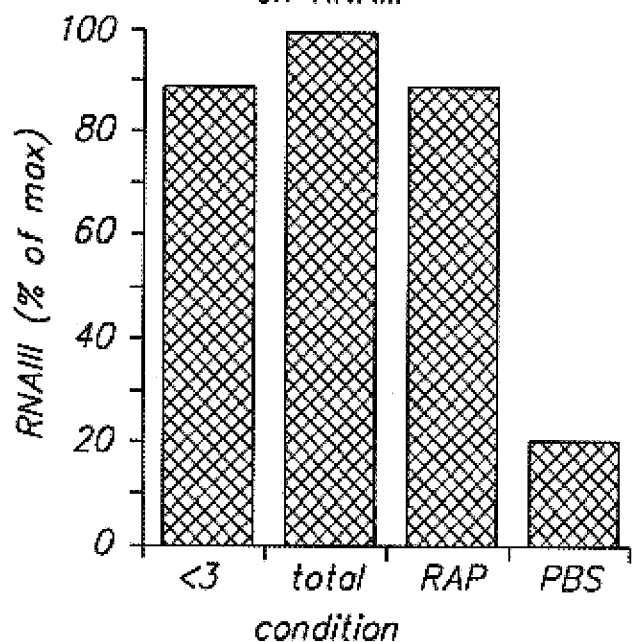
FIG. 11 is a bar graph showing RNAIII activation by the octapeptide (<3), total supernatant (total), RAP, and PBS.

Post-exponential supernatants of wild type *S. aureus* (total) were run through a 3 kDa membrane. The flowthrough containing the octapeptide encoded by agrD was collected (<3). The remaining material was used to purify RAP on a gel filtration column (RAP). Wild type early exponential *S. aureus* cells were incubated for 1 hr in PFB together with $^{32}P$, with total, the octapeptide (<3), RAP or with PBS (control). The octapeptide, which activates RNAIII production, is made by wild type *s. aureus* and is encoded by agr. Cells were collected, applied to SDS PAGE, and the gel autoradiographed (FIG. 9). The relative density of the autoradiograph bands is shown in FIG. 10. RNAII activity in the presence of the octapeptide, total supernatant, RA, and PBS was determined in parallel (FIG. 11). These data show that the octapeptide of agrD inhibits TRAP phosphorylation.

Example 5

Phosphorylation of TRAP Is Activated by RAP and Inhibited by RIP

Figure 12:
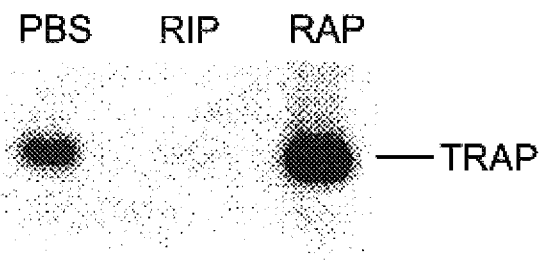
FIG. 12 is an autoradiograph showing phosphorylation of TRAP is activated in the presence of RAP and inhibited in the presence of RIP.
Figure 13:
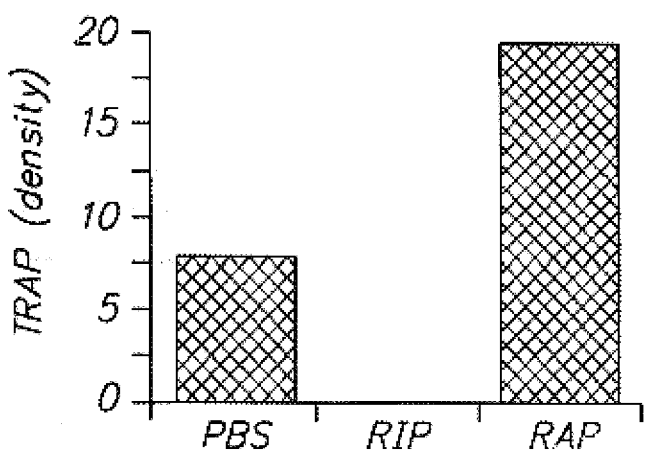
FIG. 13 is a bar graph of the density of bands of the autoradiograph of FIG. 12.
Figure 14:
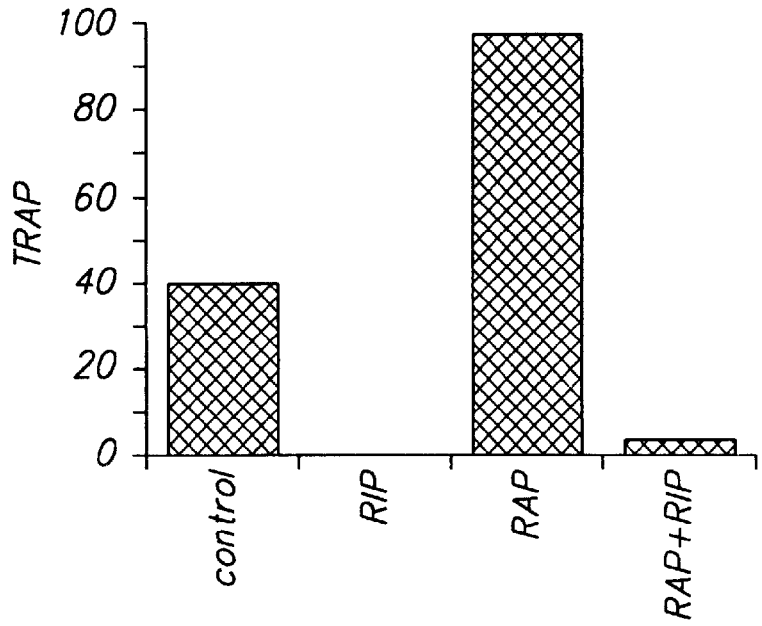
FIG. 14 is a bar graph showing the effect of RIP, RAP and the combination of RIP and RAP on TRAP phosphorylation.
Figure 15:
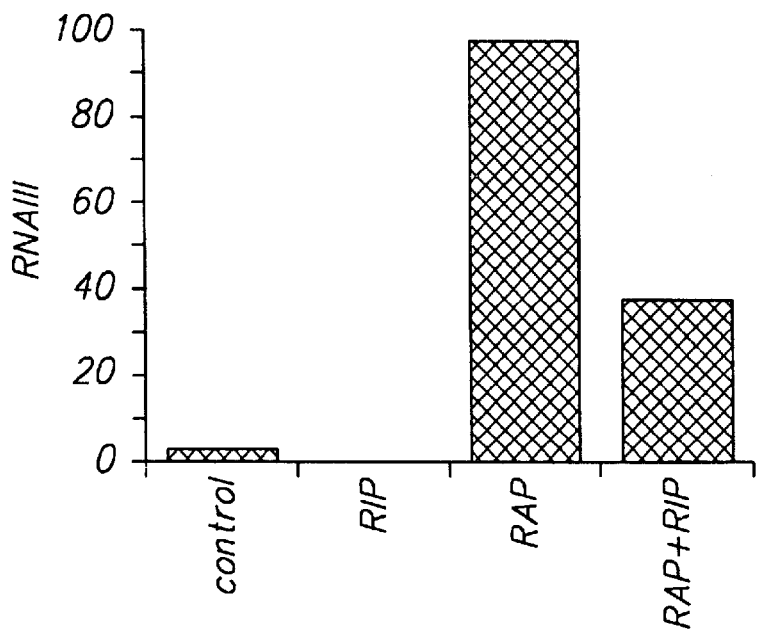
FIG. 15 is a bar graph showing the effect of RIP, RAP and the combination of RIP and RAP on transcription of RNAIII.

Wild type early exponential *S. aureus* cells were incubated in PFB with $^{32}P$ with either PBS alone, RIP, RAP, or a combination of RIP and RAP. The native RIP peptide was isolated from coagulase negative staphyloccocus strain RN833 as described in Balaban, et al., *Science* 280:438–40 (1998) and contains the sequence YSPXTNF (SEQ ID NO:3). Synthetic peptides can include peptides like YSP-WTNF (SEQ ID NO:4), YKPWTNF (SEQ ID NO:5) and YKPITNF (SEQ ID NO:6). The cells were collected, applied to SDS PAGE, the gel autoradiographed, and the relative amounts of TRAP phosphorylation and RNAIII transcription levels determined (Balaban et al. *Proc. Natl. Acad. Sci. U.S.A.* 92:1619–1623 (1995)). FIG. 12 shows the resulting autoradiograph showing the relative levels of TRAP phosphorylation. FIG. 13 is a bar graph showing the relative density of the bands associated with TRAP phosphorylation on the autoradiograph of FIG. 12. The relative levels of TRAP phosphorylation (FIG. 14) and RNAIII transcription (FIG. 15) in the presence of PBS alone (control), RIP, RAP, or RIP and RAP were also determined. These data show that TRAP phosphorylation is inhibited in the presence of RIP and enhanced in the presence of RAP. Furthermore, when RIP and RAP are combined, the presence of RIP reduces the levels of TRAP phosphorylation normally associated with RAP.

Figure 16:
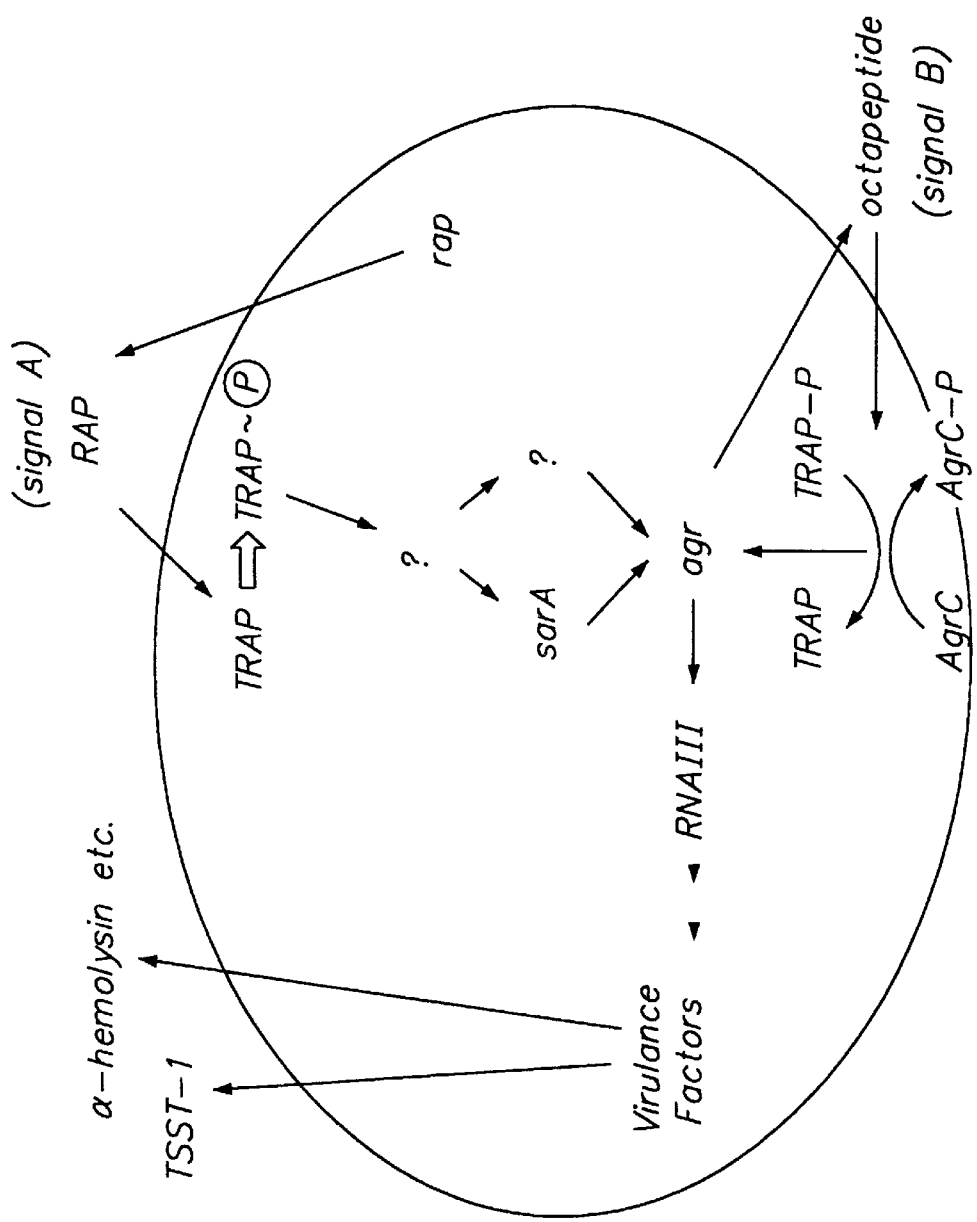
FIG. 16 is a diagram summarizing the signal transduction pathways involved in Staphylococcus virulence factor production.

Without being held to theory, the data presented in the Examples above suggest that a two step rnaiii-activation sequence (summarized in FIG. 16). During cell growth, RAP (signal A), which is independent of agr, builds to its concentration threshold. It then binds to this receptor, causing a cascade of events leading to the phosphorylation of TRAP. These events then lead to upregulation of sarA which then upregulates the agr (Chien et al. *J. Biol. Chem.* 273:2645–2652 (1998)). Once agr is activated, agrD is expressed, and an octapeptide encoded by agrD (signal B) is produced and secreted. This peptide then binds to its receptor, AgrC (Line et al. *Mol. Microbiol.* 28:655–662 (1998)), resulting in AgrC phosphorylation, downregulation of TRAP phosphorylation, upregulation of P3, and transcription of rnaiii. RNAIII induces the genes which encode various virulence factors leading to production of toxins. RIP acts as an antagonist, blocking RAP from binding to its receptor. Therefore, in the presence of RIP, TRAP is not phosphorylated, the signal transduction of virulence is not activated, RNAIII is not produced, and toxins regulated by RNAIII are not produced.

Example 6

TRAP is Histidine Phosphorylated

Figure 17:
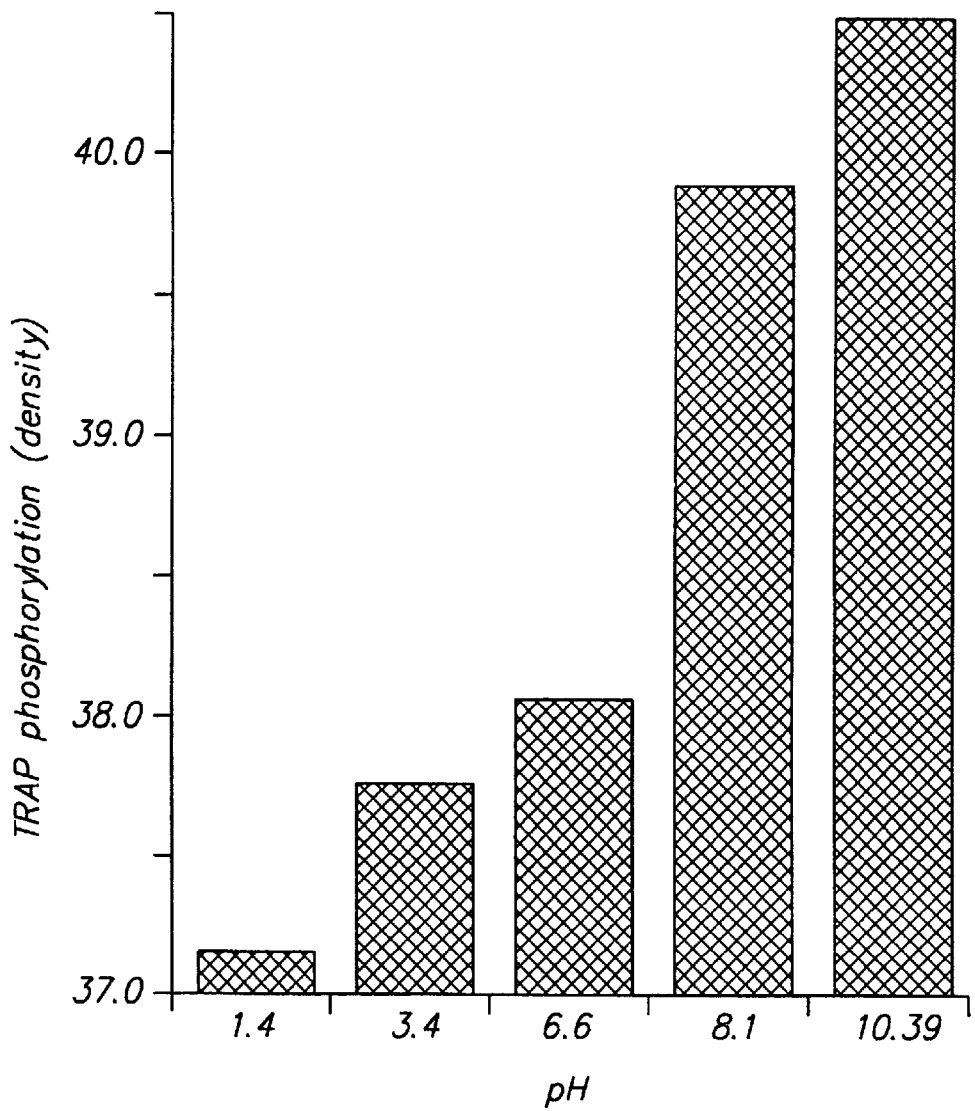
FIG. 17 is a bar graph showing that TRAP phosphorylation is stable under basic, but not acidic, conditions.

Two-component systems act through phosphorylation of the substrate domain of the sensor protein and subsequent transfer of the phosphate to an aspartate residue in the regulator protein. The initial phosphorylation is catalyzed by a protein histidine kinase domain in the sensor protein and results in an N-phosphorylated histidine residue, which is stable in alkaline conditions but not in acidic conditions (Wei et al. *Methods Enymol.* 200:388–414 (1991)). To test whether TRAP may be histidine-phosphorylated and therefore a candidate sensor to RAP, phosphorylated TRAP was tested for sensitivity to acidic and basic conditions. Phosphorylated TRAP was incubated at pH ranging from 3–10, for 10 min at room temperature. The mixture was then applied to SDS PAGE and the gel autoradiographed. Phosphorylation of TRAP was found to be stable at pH 8–10 but labile in lower pHs, suggesting N phosphorylation of a histidine (FIG. 17).

Example 7

Cloning and Sequencing of TRAP

P32-labeled TRAP was produced and purified as described in Example 1 above. A sample of isolated TRAP was separated by SDS-PAGE, and the radioactive band cut out, digested to produce fragments, and the amino acid sequence determined. Two regions within the C-terminus were sequenced. These amino acid sequences were compared with the publicly available database of the *S. aureus* genome from the Genome Sequencing Staphylococcus aureus Genome Sequencing Project website having an Internet address at www.genome.ou.edu/staph blast.html This search identified contig 876, which contained the remaining portion of the coding sequence and promoter sequence.

The sequence of TRAP and its predicted amino acid sequence are provided in the Sequence Listing as SEQ ID NOS: 1 and 2, respectively. The coding sequence extends from the initial methionine at nucleotide 64 to the stop codon at nucleotide 565. The promoter region extends from nucleotides 1 to 40, with the transcription initiation site at nucleotide 41, for a 5' UTR of nucleotides 1–62. The predicated molecular weight of encoded TRAP protein is 20,280 daltons.

Example 8

Treatment with TRAP Antibodies

Monoclonal antibodies to TRAP purified as described above are produced by the methods of Kohler and Milstein (*Nature,* 256: 495–497 (1975)) as modified by Galfre et al. (*Nature,* 266: 550–552 (1977)). 10 µg of purified TRAP antibodies are injected with CFA on first injection and with incomplete Freund's adjuvant (ICFA) on the second and third injections subcutaneously into 4-week-old immunocompetent hairless mice on days 0, 7, and 21. Control mice are either injected with the adjuvant alone or not injected at all. Vaccinated and control mice are challenged on day 31 with $1.24 \times 10^8$ SD *S. aureus* subcutaneously together with 1 mg of Cytodex™ beads to induce a local infection. The size of the lesions are measured daily.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An isolated nucleic acid molecule comprising a coding sequence encoding a polypeptide having SEQ ID NO:2.

2. The isolated nucleic acid molecule of claim 1, which consists essentially of the coding sequence encoding the polypeptide having SEQ ID NO:2.

3. The isolated nucleic acid molecule of claim 1, which consists of the coding sequence encoding the polypeptide having SEQ ID NO:2.

4. The isolated nucleic acid molecule of claim 1, wherein the polypeptide is a TRAP protein.

5. The isolated nucleic acid molecule of claim 1, wherein the coding sequence comprises the coding sequence of SEQ ID NO:1.

6. The isolated nucleic acid molecule of claim 1, wherein the coding sequence consists essentially of the coding sequence of SEQ ID NO:1.

7. The isolated nucleic acid molecule of claim 1, wherein the coding sequence consists of the coding sequence of SEQ ID NO:1.

8. The isolated nucleic acid molecule of claim 1, wherein the coding sequence comprises nucleic acid residues 63 to 565 of SEQ ID NO:1.

9. The isolated nucleic acid molecule of claim 1, wherein the coding sequence consists of nucleic acid residues 63 to 565 of SEQ ID NO:1.

10. An isolated nucleic acid molecule which comprises a sequence for expression of a polypeptide having SEQ ID NO:2.

11. The isolated nucleic acid molecule of claim 10, wherein the sequence comprises SEQ ID NO:1.

12. The isolated nucleic acid molecule of claim 10, wherein the sequence consists essentially of SEQ ID NO:1.

13. The isolated nucleic acid molecule of claim 10, wherein the sequence consists of SEQ ID NO:1.

14. The isolated nucleic acid molecule of claim 10, wherein the polypeptide is a TRAP protein.

15. The isolated nucleic acid molecule of claim 10, further comprising an operably linked promoter.

16. A recombinant vector comprising the isolated nucleic acid molecule of claim 1.

17. A recombinant vector comprising the isolated nucleic acid molecule of claim 10.

18. A host cell comprising the recombinant vector of claim 16.

19. A host cell comprising the recombinant vector of claim 17.

20. An expression cassette comprising a promoter operably linked to the isolated nucleic acid molecule of claim 1.

21. An expression cassette comprising a promoter operably linked to the isolated nucleic acid molecule of claim 10.

22. A method for producing a polypeptide which comprises culturing the host cell of claim 18 under conditions suitable for expression of the polypeptide and isolating the polypeptide.

23. A method for producing a polypeptide which comprises culturing the host cell of claim 19 under conditions suitable for expression of the polypeptide and isolating the polypeptide.

* * * * *